(12) United States Patent
Kast et al.

(10) Patent No.: US 6,242,176 B1
(45) Date of Patent: Jun. 5, 2001

(54) PAPILLOMAVIRUS CELLULAR RECEPTOR

(75) Inventors: W. Martin Kast, Willowbrook, IL (US); John D. Nieland, Munich (DE)

(73) Assignee: Loyola University of Chicago, Chicago, IL (US)

( * ) Notice: Subject to any disclaimer, the term of this patent is extended or adjusted under 35 U.S.C. 154(b) by 0 days.

(21) Appl. No.: 09/348,573

(22) Filed: Jul. 7, 1999

Related U.S. Application Data

(60) Provisional application No. 60/092,637, filed on Jul. 13, 1998.

(51) Int. Cl.[7] ............................... C12Q 3/00; C12N 5/06
(52) U.S. Cl. ........................ 435/5; 435/7.1; 435/7.24; 435/345; 435/343; 435/343.2; 435/343.1; 436/548
(58) Field of Search .............................. 435/5, 7.1, 7.24, 435/345, 343, 343.2, 343.1; 436/548

(56) References Cited

FOREIGN PATENT DOCUMENTS

WO 94/00152  1/1994  (WO) .

OTHER PUBLICATIONS

Barnett et al. *Antimicrobial Agents and Chemotherapy*, 40(2): 470–472 (1996).
Hussain et al. *AIDS 1991*, 5(9): 1089–1094 (1991).
Hussain et al. *Immunology*, 85: 475–484 (1995).
Hussain et al. *Clin. Exp. Immunol.*, 90: 530–538 (1992).
Liu et al. *Virology*, 227: 474–483 (1997).
Mansfield et al. *Biochemical Society Transactions*, 25(2): 709–714 (1997).
McCall et al. *Molecular Immunology*, 36: 433–445 (1999).
Theuer et al. *The American Journal of Surgery*, 166: 284–288 (1993).
Evander et al. *Journal of Virology*, 71(3), 2449–2456 (1997).
Müller et al., *Journal of Virology*, 69, 948–954 (1995).
Qi et al., *Virology* , 216, 35–45 (1996).
Roden et al., *Journal of Virology*, 69 (8), 5147–5151 (1995).
Roden et al., *Journal of Virology*, 68, 7260–7266 (1994).
Volpers et al., *Journal of Virology*, 69(6), 3258–3264 (1995).
Zhou et al., *Virology*, 214, 167–176 (1995).

*Primary Examiner*—Ali R. Salimi
(74) *Attorney, Agent, or Firm*—Leydig, Voit & Mayer, Ltd.

(57) ABSTRACT

The present invention provides methods and reagents for treating or preventing papillomavirus infection. In one aspect, the invention provides reagents and methods for attenuating the ability of papillomavirus to bind to cells by blocking access of papillomavirus to its cellular receptor. In another aspect, the invention provides reagents and methods for attenuating the ability of papillomavirus to infect cells by reducing the free titer of papillomavirus. In yet another aspect, the invention provides a complex comprising a biologically active substance and a ligand that recognizes CD16 and a method of delivering a biologically active substance to an papillomavirus-infected cell using the complex.

5 Claims, No Drawings

PAPILLOMAVIRUS CELLULAR RECEPTOR

This application claims the benefit of the provisional U.S. application Ser. No. 60/092,637 filed Jul. 13, 1998

STATEMENT AS TO RIGHTS TO INVENTIONS MADE UNDER FEDERALLY SPONSORED RESEARCH AND DEVELOPMENT

This invention was made with Government support under Grant Number RO1 CA74397 awarded by the National Institutes of Health. The United States Government may have certain rights in this invention.

TECHNICAL FIELD OF THE INVENTION

The present invention relates to methods and reagents for treating or preventing papillomavirus infection.

BACKGROUND OF THE INVENTION

Papillomavirus are causative agents for several types of epithelial and mucosal diseases. Of particular concern is that certain strains of papillomavirus are associated with cervical and penile cancers (see, e.g., Iwasawa et al., J. Urol., 149, 59–63 (1993); Koutsky et al., N. Engl. J. Med., 327, 1272–78 (1992)). Considerable efforts, therefore, are underway to prevent the spread of this virus by developing a prophylactic vaccine and novel treatments for papillomavirus-induced lesions (see, e.g., Cason et al., Vaccine, 11, 603–11 (1993); Crawford, Cancer Surv., 16, 215–29 (1993)). Such efforts, however, have been hampered by the particular difficulties of working with papillomavirus in vitro. To complete its life cycle, papillomavirus requires its host cell to undergo a differentiation event. Currently, no in vitro culture system duplicates this state adequately to permit efficient papillomavirus growth in vitro.

Papillomaviruses are nonenveloped double-stranded DNA viruses about 55 nm in diameter with an approximately 8-kb genome in a nucleohistone core (Baker et al., Biophys J. 60, 1445–56 (1991)). The capsids include two viral proteins (L1 and L2) of about 55 kDa and 75 kDa, respectively (Larson et al., J. Virol., 61, 3596–3601 (1987)). L1 is the major capsid protein, and it is arranged in 72 pentameres within the capsid. In fact, L1 has the ability to self-assemble into virus-like particles (VLPs) upon production of the L1 protein in eukaryotic cells (see, e.g., Hagensee et al., J. Virol., 67, 315–22 (1993); Kirnbauer et al., J. Virol., 67, 6929–36 (1993)). The function and position of L2 within the virion are not clear, although the protein is assembled with L1 into VLPs when coexpressed in cells.

Because of the lack of suitable papillomavirus culture conditions, VLPs typically are used for in vitro studies of papillomavirus infection, as opposed to intact papillomavirus (see, e.g., Roden et al., J. Virol., 68, 7260–66 (1994); Volpers et al., J. Virol., 69, 3258–64 (1995)). Using VLPs, it is now thought that a putative cell receptor for papillomavirus is expressed across a wide range of cell types and is highly conserved between a diverse group of organisms (see, e.g., Müller et al., J Virol., 69, 948–54 (1995); Volpers et al., supra; Roden et al., supra). Currently, little is understood about papillomavirus infection, particularly the identity of a cell surface receptor recognizing papillomavirus.

In view of the foregoing problems, there exists a need for methods and reagents for treating or preventing papillomavirus infection.

BRIEF SUMMARY OF THE INVENTION

The present invention is predicated, at least in part, on the discovery that papillomavirus selectively binds the CD16 protein present in a variety of cells. Using this discovery, the present invention provides methods and reagents for treating or preventing papillomavirus infection. In one aspect, the present invention provides reagents and methods for attenuating the ability of papillomavirus to bind to cells by blocking access of papillomavirus to its cellular receptor. In another aspect, the present invention provides a method of attenuating the ability of papillomavirus to infect cells by reducing the free titer of papillomavirus. In another aspect, the present invention provides a complex comprising a biologically active substance and a ligand that recognizes CD16 and a method of delivering a biologically active substance to an HVP-infected cell using the complex. These and other advantages of our invention, as well as additional inventive features, will be apparent from the following detailed description.

DETAILED DESCRIPTION OF THE INVENTION

The present invention provides methods and reagents for treating or preventing papillomavirus infection. In one aspect, the method attenuates the ability of papillomavirus to bind cells. One method of attenuating the ability of papillomavirus to bind cells is to expose the cells to a ligand that recognizes CD16 under conditions sufficient for the ligand to bind CD16. The bound ligand interferes with subsequent interaction between papillomavirus and the CD16 molecules; thus, by such treatment, the ability of papillomavirus to subsequently bind cells is attenuated.

In this context, the ligand is present on any molecule suitable for blocking the interaction between papillomavirus and the bound CD16 protein. While many types of molecules can provide the ligand, generally the ligand is present as part of a protein. For example, the ligand can be an antibody recognizing an epitope on CD16. In other embodiments, the ligand is on a protein including an external domain of an papillomavirus capsid protein (e.g., L1, L2, or a soluble derivative of L1 or L2 retaining an extracellular domain). The residues that comprise the ligand in a protein need not necessarily be contiguous in the chain of amino acids that make up the protein. In other words, the ligand can be generated by the particular conformation of the protein, e.g., through folding of the protein in such a way as to bring contiguous and/or noncontiguous sequences into mutual proximity. Such proteinatious species can be synthesized using standard direct peptide synthesizing techniques (see, e.g., Bodanszky, Principles of Peptide Synthesis (Springer-Verlag, Heidelberg: 1984)), such as via solid-phase synthesis (see, e.g., Merrifield, J Am. Chem. Soc., 85, 2149–54 (1963); Barany et al., Int. J Peptide Protein Res., 30, 705–739 (1987); and U.S. Pat. No. 5,424,398). Alternatively, such modified proteins can be chemically crosslinked, and a variety of cross-linking agents are known in the art and widely available (e.g., succinimidyl or maleimidyl cross-linkers). Methods for conjugating peptides and polyamines are also well-known in the art (see, e.g., Staros, Biochem., 21, 3990 (1982)). Alternatively, a DNA fragment encoding the protein can be subcloned into an appropriate vector using well known molecular genetic techniques. The fragment is then transcribed and the peptide subsequently translated in vitro within a host cell. Any appropriate expression vector (see, e.g., Pouwels et al., Cloning Vectors: A Laboratory Manual (Elsevier, NY: 1985)) and corresponding suitable host cells can be employed for production of recombinant peptides. Expression hosts include, but are not limited to, bacterial species, mammalian or insect host cell systems including baculovirus systems (e.g., as described by Luckow et al., Bio/Technology, 6, 47 (1988)), and established cell lines such 293, COS-7, C 127, 3T3, CHO, HeLa, BHK, etc. From such cells, the modified chimeric proteins can be harvested by standard techniques.

The ligand is exposed to the cells, e.g., under conditions suitable for the ligand to bind the CD16 protein. For example, for cells in vitro, the ligand-bearing molecules can be added to the cell culture for a time sufficient for them to bind the CD16 molecules on the cells. For cells in vivo, the ligand-bearing molecules can be supplied in a pharmacologically acceptable carrier (e.g., a solution, gel, magma, or salve). In this regard, the ligand can be delivered topically to cells within a discrete organ or tissue or systemically to attenuate papillomavirus infection on a more wide-spread scale.

The ligand recognizing CD16 is exposed to the cells under conditions sufficient for the ligand to bind the cells. The concentration of ligand, as well as the conditions required for efficient binding, will depend on the type of ligand employed and location of delivery. However, it is within the routine skill in the art to investigate the kinetic profile of such ligands in advance of an application.

In accordance with the present invention, another method of attenuating the ability of papillomavirus to infect cells is to reduce the free titer of papillomavirus. In the context of the invention, this can be achieved by exposing papillomavirus to a ligand that recognizes the surface of an papillomavirus under conditions sufficient for the ligand to bind the papillomavirus. The resultant papillomavirus/ligand complex is less able to infect cells than unbound papillomavirus (i.e., it forms a noninfective complex).

In this context, the ligand can be present on any molecule suitable for interacting with papillomavirus. While many types of molecules can provide the ligand, generally the ligand is present as part of a protein. For example, the ligand can be an antibody recognizing the surface of the papillomavirus virion (or one of the two capsid proteins). Many such antibodies are known in the art, and some are commercially available. In other embodiments, the ligand is present in a protein including an external domain from the CD16 protein. For example, soluble derivatives of the CD16 protein are disclosed in published international application WO 89/11490. Where the ligand is proteinatious, the protein can be manufactured by any suitable method, such as the methods discussed above.

The ligand recognizing papillomavirus is exposed to the virus under conditions suitable for the ligand to bind papillomavirus. For example, to attenuate infection of cells in vitro, the ligand can be added to the culture solution. To attenuate in vivo infection, the papillomavirus-ligand can be supplied in a pharmacologically acceptable carrier (e.g., a solution, gel, magma, or salve). In this regard, for example, a pharmacologically-acceptable carrier containing the ligand recognizing papillomavirus can be injected into a patient (e.g., intravenously, subcutaneously, etc.) or applied to the skin or mucosa to reduce the titer of papillomavirus. Alternatively, the ligand recognizing papillomavirus can attenuate infection of cells within a discrete organ or tissue (e.g., a tumor) by supplying the carrier containing the ligand to the tissue.

This strategy can also be employed to reduce the transmission of papillomavirus. For example, as papillomavirus is a sexually-transmitted virus, the ligand recognizing papillomavirus can be applied vaginally, for example in a creme, douche, sponge or other suitable carrier. Alternatively, a carrier containing the ligand can be used to coat a condom or similar device to attenuate viral transmission between individuals.

To reduce viral titer, the ligand recognizing the papillomavirus surface is exposed to the papillomavirus under conditions sufficient for the ligand to bind the papillomavirus. The concentration of ligand, as well as the conditions required for efficient binding, will depend on the type of ligand employed and location of delivery. However, it is within the routine skill in the art to investigate the kinetic profile of such ligands in advance of an application.

Regardless of the type of ligand employed (e.g., either a ligand recognizing papillomavirus or a ligand recognizing CD16 ), the present inventive method attenuates the ability of the virus to infect cells. In many cases, the ability of papillomavirus to bind a population of cells is reduced by at least an order of magnitude. Typically, the method can substantially reduce, or even practically eliminate, the ability of the virus to bind to, and therefore infect, cells. However, even in protocols in which some residual viral infection still occurs, the method is a useful prophylaxis or therapy for papillomavirus-associated disorders. Indeed, any reduction in the incidence of viral infection renders it less likely that a given papillomavirus infection will spread or be transmitted between individuals. Moreover, protocols, such as the inventive method, that attenuate viral infection can be used in combination with other regimens to combat papillomavirus infective diseases.

Aside from attenuating the ability of papillomavirus to infect cells, the discovery that papillomavirus binds CD16 affords a method of delivering a pharmacologically active substance to a papillomavirus-infected cell. This method uses a complex including a pharmacologically active substance and a ligand recognizing CD16. The complex is exposed to the papillomavirus-infected cells under conditions sufficient for the ligand to bind CD16 on the cells. The pharmacologically active substance is thus brought into proximity to, and delivered to, the infected cell. The use of this method permits the targeted delivery of the pharmacologically active substance to the infected cells. This permits the employment of relatively high concentrations of many pharmacologically active agents to be delivered to the infected cells without many of the concomitant side effects attributed to the activity of such agents in noninfected cells.

For use in this method, the complex includes at least a ligand recognizing CD16 and a pharmacologically active substance. In this regard, the ligand is present on any molecule suitable for interacting with the CD16 protein present on papillomavirus-infected cells, such as the molecules described above. The complex is delivered to the infected cells similarly to the manner described above.

Within the complex, the pharmacologically active substance can be any compound that exerts a biological effect on the infected cells. For example, for treating tumors (e.g., cervical or penile cancers), warts, or other papillomavirus-related lesions, the pharmacologically active substance can be a medicament, cytotoxin, chemotherapeutic agent, radioactive agent, etc.

In other embodiments, the pharmacologically active substance is a gene encoding a bioactive molecule. In such circumstances, the complex delivers the gene to the infected cells such that the cells internalize the gene and express it to produce the bioactive molecule. For combating tumors associated with papillomavirus infection, the gene can encode a cytokine (e.g., tumor necrosis factor (TNF), TGF-α, TGF-β, interleukins (IL) such as IL-1, IL-2, IL-3, etc., GM-CSF, G-CSF, M-CSF, co-stimulatory factor B7, etc.), a protein that promotes cell death or an enzyme that converts a prodrug into a cytotoxin (e.g., HSV-tk, cytosine deaminase, xanthine/guanine phosphoribosyltransferase, cytochrome p450 2B1, etc.). Still other bioactive molecules are RNA species having sequences antisense to portions of papillomavirus genes (e.g., the genes encoding L1, L2).

The complex can be formed in any suitable manner. In one embodiment, the complex can be proteinatious (e.g., a chimeric protein having the papillomavirus ligand as a first domain and the pharmacologically active substance as a second domain). For example, the complex can comprise all or a portion of the CD16 molecule fused to a toxin. A preferred chimeric complex includes a soluble portion of the CD16 molecule fused to a portion of the Pseudomonas endotoxin A (see, e.g., U.S. Pat. No. 5,587,455). Such proteinatious agents can be manufactured by any appropriate method, such as those discussed above.

Many such complexes include non-proteinatious components. For example, such a complex can incorporate nucleic acids (e.g., encoding the genes described above). In other embodiments, the complex can include an agent for tethering the pharmacologically active substance to the ligand. For example incorporating lipids into the complex (e.g., in the form of liposomes) enhances cellular uptake of many types of pharmacologically active agents, especially nucleic acids. The use of such lipids is especially preferred when the ligand component of the complex is of viral origin (e.g., L1, L2, a VLP, etc.) (see, e.g., Innes et al., *J Virol.*, 64, 957–61 (1990); Morishaita et al., *Hypertension*, 21, 894–99 1993); U.S. Pat. 5,635,380). Where a liposome is employed in the complex, and where a nucleic acid is the pharmacologically active agent, preferably the liposome contains cationic lipids, but can contain neutral lipids as well. Preferred cationic lipids include LIPOFECTIN (DOTMA) (Gibco BRL), LIPOFECTMINE (Gibco BRL), and DOTAP (Boeringer-Mannheim), and others are known in the art (see, e.g., U.S. Pat. No. 5,736,392).

Such complexes including non-proteinatious components can be created by mixing the ligand with the lipid and/or nucleic acid and allowing the complexes to form. The mixing can occur, for example, in a serum-free culture medium, and can occur under any suitable temperature.

While it is believed that one of skill in the art is fully able to practice the present invention after reading the foregoing detailed description, the following examples are set forth to further illustrate some of its features. In particular, these examples demonstrate that papillomavirus can selectively bind the CD16 cell-surface molecule, that a ligand recognizing the CD16 cell surface molecule can block papillomavirus attachment to cells, that various papillomavirus-induced tumors express the CD16 molecule, that CD16 expression is associated with HPV binding in vivo, and that HPV binds cells poorly unless they express CD16.

The procedures employed in these examples, such as affinity chromatography, Southern blots, PCR, DNA sequencing, vector construction (including DNA extraction, isolation, restriction digestion, ligation, etc.), cell culture (including antibiotic selection), transfection of cells, protein assays (Western blotting, immunoprecipitation, immunofluorescence), in situ hybridization, etc., are techniques routinely performed by those of skill in the art (see generally Sambrook et al., *Molecular Cloning, A Laboratory Manual*, Cold Spring Harbor Laboratory, Cold Spring Harbor, N.Y. 1989)). Accordingly, in the interest of brevity, the basic experimental protocols are not discussed in detail. As these examples are included for purely illustrative purposes, they should not be construed to limit the scope of the invention in any respect.

EXAMPLE 1

This example demonstrates that CD16 is a cellular receptor for papillomavirus.

The ability of a ligand recognizing the CD16 protein to block papillomavirus binding was assayed by FACS analysis using cocktails of antibodies recognizing various cell surface proteins. Single cell suspensions of human peripheral blood lymphocytes obtained with the consent of a donor were created.

Papillomavirus binding was assessed using papillomavirus L1 /L2 VLPs (Greenstone et al., *Proc. Nat. Acad. Sci. USA*, 95, 1800–05 (1998)). To assess signal, these VLPs were biotinylated by incubating them with N-hydroxy-succinimide-biotin for one hour at room temperature. The VLPs were dialyzed against standard phosphate-buffered saline for four hours and then stored at −80° C. for later use. Biotinylation was assessed using a sandwich ELISA. At a 100-fold dilution, biotinylated VLPs registered positive, while control VLPs exhibited little absorption signal.

The cell populations were incubated on ice with the biotinylated VLPs for two hours. Following the incubation, populations of cells were incubated with streptavidin-APC and the various antibody cocktails indicated in Table 1. Following this second incubation, the cells were exposed to labeled secondary antibody (rat or mouse FITC-conjugated Ig). In blocking experiments, the cells were pre-incubated with antibodies for one hour on ice. The antibodies employed recognized, respectively, CD16, CD21, CD23, CD32, CD64, $\alpha 6$ integrin, and $\beta 4$ integrin. Fluorescence was assessed and quantified using a FACS-Calibur with CELLQUEST software (Becton-Dickinson). The number of cells gated for MCH class II and bound to biotinylated VLP were counted.

The data revealed that only when the anti-CD16 antibody was absent from the cocktail did the papillomavirus VLPs bind to the cells with wild-type efficiency. Significantly, these results demonstrate that exposing cells to a ligand recognizing CD16 (e.g., the anti-CD16 antibody used in these experiments) attenuates papillomavirus binding. Importantly, the results indicate that interfering with the interaction between the VLPs and the 6 integrin with the $\alpha 6$ antibody had no effect on viral binding. This result is surprising because it is inconsistent with a prior suggestion that the $\alpha 6$ integrin may be a papillomavirus receptor (Evander et al., *J. Virol.*, 71(3), 2449–56 (1997)).

EXAMPLE 2

This example demonstrates that cells associated with papillomavirus infection express CD16 on the cell surface.

Various cell lines (i.e., RD cells (a monkey kidney cell line), HeLa cells (a human papillomavirus strain 18-expressing cervical cancer cell line), CV1 cells (a monkey kidney cell line), BB49 cells (a human papillomavirus strain 6-expressing head and neck cancer cell line), Caski cells (a human papillomavirus strain 16-expressing cervical cancer cell line), and Epstein-Barr Virus-transformed cells)) were assayed for CD16 expression using an antibody recognizing CD16. The total number of cells in each population, and the number of such cells expressing CD16, were measured by FACS analysis as described above.

The results revealed that the number of cells expressing CD16 approximated the number of cells in each population, indicating that papillomavirus-infected cells express CD16. These results are consistent with published immunohistochemical data demonstrating that CD16 is expressed in tissue associated with HPV lesions, but not expressed in other tissues (compare Hussain et al., *AIDS*, 5, 1089–94 (1991), Hussain et al., *Clin Exp. Immunol*, 90, 530–38 (1992), and Hussain et al., *Immunology*, 85, 475–84 (1995)).

EXAMPLE 3

This example demonstrates that CD16 expression correlates with HPV binding in situ.

Frozen sections of human foreskin epithelium were incubated with either biotinylated HPV16 L1/L2 VLPs, an anti-human CD16 monoclonal antibody, an anti-human α6 integrin, or an anti-human β4 integrin. The sections exposed to VLPs were then incubated with peroxidase-labeled streptavidin, and the sections exposed to the antibodies were incubated with peroxidase-labeled secondary antibodies. Subsequently, each section was developed with peroxidase substrate.

Histological examination of each section revealed α6 and β4 integrin staining in a well-defined deep stratum of dermis, stratum basale, well away from the surface of the foreskin. Conversely, CD16 staining was observed in a discrete layer of tissue at the surface of the foreskin. HPV particles were detected only in the region in which CD16 was detected, and not in the regions in which α6 and β4 integrin were detected. This result is surprising because it is inconsistent with a prior suggestion that α6 or β4 integrins may be papillomavirus receptors (Evander et al., supra).

EXAMPLE 4

This example demonstrates that HPV binding in vivo is reduced in the absence of CD16.

Biotinylated HPV16 L1/L2 VLPs were incubated with splenocytes from either C57 B1/6 or CD16 knockout mice. Non-biotinylated HPV16 L1/L2 VLPs were used as a control. After incubation, the cells were washed, and VLP binding was assayed using allophycocyanin-labeled streptavidin. Fluorescence was assessed using a Becton Dickinson FacsCalibur running CellQuest software.

The data revealed that the VLPs bound the knockout cells with only about half the efficiency to which they bound wild-type cells expressing CD16. These results demonstrate that CD16 is required for high-efficiency papillomavirus infection.

All of the references cited herein, including patents, patent applications, and publications, are hereby incorporated in their entireties by reference.

While the present invention has been described with an emphasis upon preferred embodiments and illustrative examples, it will be obvious to those of ordinary skill in the art that variations of the preferred embodiments may be used and that the present invention can be practiced otherwise than as specifically described herein. Accordingly, the present invention includes all modifications encompassed within the spirit and scope of the invention as defined by the following claims.

What is claimed is:

1. A method of attenuating the ability of papillomavirus to bind cells, said method comprising exposing cells to a ligand that recognizes CD16 under conditions sufficient for said ligand to bind said CD16, whereby the ability of said papillomavirus to subsequently bind said cells is attenuated.

2. The method of claim 1, wherein said ligand is an antibody recognizing an epitope on said CD16.

3. The method of claim 1, wherein said ligand is a protein comprising an external domain of a papillomavirus capsid protein.

4. A method of attenuating the ability of papillomavirus to bind cells, said method comprising exposing papillomavirus to a ligand that recognizes the surface of a papillomavirus under conditions sufficient for said agent to bind said papillomavirus to form a noninfective complex.

5. The method of claim 4, wherein said ligand is a soluble CD16 peptide.

* * * * *